United States Patent [19]

Bartzokis et al.

[11] Patent Number: 5,322,682
[45] Date of Patent: Jun. 21, 1994

[54] METHOD FOR QUANTITATIVELY MEASURING AND MAPPING STORED IRON IN TISSUE USING MRI

[75] Inventors: George Bartzokis; Carolanne K. Phelan, both of Los Angeles, Calif.

[73] Assignee: The Regents of the University of California, Oakland, Calif.

[21] Appl. No.: 926,245

[22] Filed: Aug. 6, 1992

[51] Int. Cl.$^5$ .................. G01N 24/08; A61K 33/26; G01V 3/00

[52] U.S. Cl. .................. 424/9; 128/653.2; 128/653.4; 436/173; 324/300; 324/307; 324/308; 424/646

[58] Field of Search ............... 424/9, 646; 128/653.2, 128/653.4, 654; 436/173; 324/300, 307, 308

[56] References Cited

U.S. PATENT DOCUMENTS

| | | | |
|---|---|---|---|
| 4,477,777 | 10/1984 | Gordon | 324/300 |
| 4,735,796 | 4/1988 | Gordon | 424/9 |
| 4,789,830 | 12/1988 | Stokar | 324/308 |
| 4,889,125 | 12/1989 | Doddrell et al. | 128/653 |
| 4,889,126 | 12/1989 | Doddrell et al. | 128/653 |
| 4,984,574 | 1/1991 | Goldberg et al. | 128/653.2 |
| 5,072,732 | 12/1991 | Rapoport et al. | 128/653.2 |

OTHER PUBLICATIONS

Narayan, P. et al. Magn. Res. in Med. 11:209-220 (1989).
Neurohr, K J et al. Adv. Myocardiol. 6:158-193 (1985).
Evelhoch, J L Invest. New Drugs 7:5-12 (1989).
"Role of Iron and Ferritin in MR Imaging of the Brain: . . . ," Bizzi et al., Radiology 1990; 177:59-65.
"4-tesla sites initiate clinical MR studies," by Lori D' Agincourt, Product Development pp. 81-83, 87 & 104, Diagnostic Imaging Dec. 1991.
"Magnetic Resonance Imaging and Brain Iron . . . ," Burton P. Drayer, M.D., BNI Quarterly, vol. 3 No. 4, Fall 1987, pp. 15-30.
"MRI in basal ganglia diseases," D. Wimberger et al., J. Neural Transm (1991) [suppl] 133-140 ® by Springer-Verlag 1991.
"Dashed Hopes for MR Imaging of the Head and Neck . . . ," Editorials from the Neuroradiology Section, Dept. of Radiology, Hospital of the University of Pennsylvania, Radiology 1991; 184:25-26.
"$T_2$-Relaxometry-A Critical Investigation . . . ," Thomas Tolxdorff et al., SMRM 1988, p. 33.
"$T_2$ Values in the Human Brain: Comparison with Quantitative Assays of Iron and Ferritin[1]" Julian C. Chen, M.D. et al. Radiology 1989, pp. 521-526.
"Field Strength in Neuro-MR Imaging: A Comparison of 0.5T and 1.5T" Clifford R. Jack, Jr., et al., Journal of Computer Assisted Tomography, vol. 14, No. 4, 1990, pp. 505-513.

(List continued on next page.)

Primary Examiner—Glennon H. Hollrah
Assistant Examiner—Gary E. Hollinden
Attorney, Agent, or Firm—Daniel L. Dawes

[57] ABSTRACT

The invention provides a specific measure of iron stores in vivo using magnetic resonance imaging. $T_2$ relaxation times in both lower-to-mid field strength magnetic resonance imaging instruments and a higher field strength instrument is evaluated. $T_2$ obtained at the higher field strength instrument is subtracted from $T_2$ obtained at the lower field strength instrument. This difference, T, is then correlated with a quantitative measure of the iron stores in vivo in the scanned tissue. A two-dimensional or multidimensional map of the scanned tissue is then constructed on the basis of T to visually identify different tissue types as being normal or abnormal, either through a visual determination based on gray scales or a numeric comparison based on quantitative measure. The introduction of artificial or nonbiological substances as opposed to natural ferritin, is permitted for further diagnostic use by application of this methodology.

27 Claims, 3 Drawing Sheets

OTHER PUBLICATIONS

"Nuclear Relaxation of Human Brain Gray and White Matter: Analysis of Field Dependence and Implications for MRI" Helmut W. Fisher et al., Magnetic Resonance in Medicine 16, 317-334 (1990).

"Are Hepatic and Muscle $T_2$ Values Different at 0.5 and 1.5 Tesla?" Magnetic Resonance Imaging, vol. 7, pp. 363-367, 1989, Michael E. Bernardino et al.

"Biological Significance of Iron-Related Magnetic Resonance Imaging Changes in the Brain" Arch Neurol--vol. 49, Jul. 1992, Jesus Pujol, M.D. et al.

"Transverse Relaxation of Solvent Protons Induced by Mangetized Spheres: Application to Ferritin, Erythrocytes, and Magnetite" Pierre Gillis et al. Magnetic Resonance in Medicine 5, 323-345 (1987).

"MR Imaging of Intracerebral Blood: Diversity in the Temporal Pattern at 0.5 1.0T" Amer Zyed et al., AJNR 12:469-474, May/Jun. 1991;AJR 157:133-138 Jul. 1991.

"NMR Relaxation Times of Blood: Dependence on Field Strength, Oxidation State, and Cell Integrity" John M. Gomori et al., J Comput Assit Tomogr, vol. 11, No. 4 1987, pp. 684-690.

"Does signal-attenuation on high-field $T_2$-weighted MRI of the brain reflect regional cerebral iron deposition? Observations on the relationship between regional cerebral water proton $T_2$ values and iron levels" D. J. Brooks et al., Journal of Neurology, Neurosurgery, and Psychiatry 1989; 52:108-111.

"Notes On the Origin of Paramagnetic Inhomogeneity Effects in Whole Blood" N. A. Watwiyoff et al., Magnetic Resonance in Medicine 20, 144-150 (1991).

"$T_2$ Estimates in Healthy and Diseased Brain Tissue: A Comparison Using Various MR Pulse Sequences[1]" Robert H. Darwin et al., Radiology 1986;160:375-381.

"Reproducibility of Relaxation and Spin-Density Parameters in Phantoms and the Human Brain Measured by MR Imaging at 1.5T" Robert K. Breger et al., Magnetic Resonance in Medicine 3, 649-662 (1986).

"In-vivo Measurements of MRI Tissue Parameters at Various Magnetic Field Strengths" By Jyh-Horng Chen, Dissertation, Univ. of Calif. Berkeley with San Francisco (1991).

"MR Imaging of Cerebral Hematomas at Different Field Strengths: Theory and Applications" Rodney A. Brooks et al., J. Cpmput Assist Tomogr vol. 13 No. 2 1989 pp. 194-206.

"Hepatic Iron Overload: Quantitive MR Imaging[1]" John M. Gomori et al., Radiology 1991;179;367-369.

"The Role of Ferritin and Hemosiderin in the MR Appearance of Cerebral Hemorrhage: A Histopathologic Biochemical Study in Rats" Keith R. Thulborn et al., AJNR 11:291-297, Mar./Apr. 1990; AJR 154:May 1990.

"Diffusion-Weighted MR Imaging of Acute Stroke: Correlation with $T_2$-Weighted and Magnetic Susceptibility-Enhanced MR Imaging in Cats" M. E. Moseley et al., AJNR 11:423-429, May/Jun. 1990.

"Late Onset Familial Hallervorden-Spatz Disease: MR Findings in Two Sisters" Paolo Ambrosetto, et al., AJNR 13:394-396, Jan/Feb 1992 1095-6108/92/13-01-0394 ©American Society of Neuroradiology.

"MR Imaging of Parkinson Disease with Spin-Echo and Gradient-Echo Sequences" Bruce H. Braffman[1,2], AJR 152:159-165, Jan. 1989.

"Brain Iron in Patients with Parkinson Disease: MR Visualization Using Gradient Modification" Joseph F. Norfray[1] et al., AJNR 9:237-240, Mar./Apr. 1988.

"Study of Movement Disorders and Brain Iron by MR" J. Neal Rutledge[1,2] et al., AJNR 8:397-411, May/Jun. 1987.

"Magnetic Resonance Imaging in Huntington Disease" J. Thayer Simmons et al., AJNR 7:25-28, Jan./Feb. 1986.

"Mechanisms of MR Signal Alteration by Acute Intracerebral Blood: Old Concepts New Theories" L. Anne Hayman et al., AJNR 12:899-907, Sep./Oct. 1991.

"Detection of Acute Intracerebral Hemorrhage on MR Imaging: Ineffectiveness of Prolonged Interecho Interval Pulse Sequences" Weingarten et al., AJNR 12:475-479, May/Jun. 1991.

"Clinically Documented Hemorrhage in Cerebral Arteriovenous Malfunctions: MR Characteristics" Phylliss M. Chappell et al., Radiology 1992; 183:719-724.

"Parkinson Plus Syndrome: Diagnosis Using High Field MR Imaging of Brain Iron" Burton P. Drayer et al., Radiology 1986; 159:493-498.

"Imaging of the Aging Brain Part II. Pathologic Conditions[1]" Burton P. Drayer, MD, Radiology 1988; 166:797-806.

"Imaging of the Aging Brain Part I. Normal Findings[1]" Burton P. Drayer, MD, Radiology 1988; 166:785-796.

(List continued on next page.)

OTHER PUBLICATIONS

"Wilson Disease of the Brain: MR Imaging[1]" Alex M. Aisen et al., Radiology 1985; 157:137–141.

"Multiple System Atrophy (Shy-Drager Syndrome): MR Imaging[1]" Behram Pastakia et al., Radiology 1986; 159:499–502.

¢Mangetic Resonance Imaging of Transfusional Hemosiderosis Complicating Thalassemia Major[1]" Robert C. Brasch et al., Radiology 1984; 150:767–771.

"Intracranial Hematomas: Imaging by High-Field MR[1]" John M. Comori, et al., Radiology 1985; 157:87–93.

"Magnetic Resonance Imaging of the Midbrain in Parkinson's Disease" J. R. Duguid et al., Annals of Neurology vol. 20 No. 6 Dec. 1986, pp. 744–747.

"Nuclear Magnetic Resonance Imaging in Movement Disorders" Steven A. Lukes, et al, Annals of Neurology vol. 13 No. 6 Jun. 1983 pp. 690–691.

"High-Field MR Imaging of Superficial Siderosis of the Central Nervous System" John M. Gomori et al., J Comput Assist Tomogr vol. 9 No. 5 1985 pp. 972–975.

"Brain Iron in Progressive Supranuclear Palsy: Clinical, Magnetic Resonance Imaging . . . " C. Edward Coffey et al., Journal of Neuropsychiatry vol. 1 No. 4 Fall 1989.

"MRI in autonomic failure" Robert T. Brown et al., Journal of Neurology, Neurosurgery and Psychiatry 1987; 50:913–914.

"Magnetic Resonance Imaging of Dystonic States" J. Neal Rutledge et al., Advances in Neurology, vol. 50 pp. 265–275 (1988).

"MRI of Brain Iron" Burton Drayer[1,2]" et al., ARJ 147:103–110 Jul. 1986.

"Assessment of Tissue Iron Overload by Nuclear Magnetic Resonance Imaging" Johnston et al., American Journal of Medicine vol. 87 Jul. 1989 pp. 40–47.

"Nuclear Magnetic Resonance of Iron and Copper Disease States" Val M. Runge et al., ARJ 141:943–948, Nov. 1983.

"Early Detection of Regional Cerebral Ischemia in Cats: Comparison of Difusion- and T2-Weighted MRI and Spectroscopy" M. E. Moseley et al., Magnetic Resonance in Medicine 14, 330–346 (1990).

"Lesions of the putamen: Their relevance to dystonia" R. D. Fross et al., Neurology 1987; 37:1125–1129.

"MR Imaging of Cerebral Hematomas at Different Field Strengths: Theory and Applications" Rodney A. Brooks et al., J Comput Assist Tomogr 13(2):194–206 1989.

"Magnetic resonance imaging of stationary blood: A review" Rodney A. Brooks et al., Med. Phys. 14(6), Nov./Dec. 1987 pp. 903–913.

"Striatonigral degeneration: Clinical, MRI, and pathologic correlation" Christopher O'Brien et al., Neurology 1990; 40:710–711 (1990).

"Magnetic resonance imaging in pathologically proven Hallervorden-Spatz disease" Schaffert et al., Neurology 39 Mar. 1989 pp. 440–442.

"NMR Imaging of the Liver in Two Cases of Iron Overload" Leung et al., J Comput Asst Tomogr 8(3):446–449 Jun. 1984.

"Magnetic Resonance Imaging and Spectroscopy of Hepatic Iron Overload" Stark et al., Radiology 1985; 154: 137–142.

"Low Paramagnetic-Ion Content in Cancer Cells: Its Significance in Cancer Detection by Magnetic Resonance Imaging" Ling et al., Physiol. Chem. Phys. & Med. NMR (1990)22:1–14.

"Parenchymal versus Reticuloendothelial Iron Overload in the Liver: Distinction with MR Imaging" Siegelman et al., Radiology 1991; 179:361–366.

"The Effects of Iron Oxides on Proton Relaxivity" Josephson et al., Magnetic Resonance Imaging vol. 6 pp. 647–653, 1988.

"Quantitation of MR Relaxation Effects of Iron Oxide Particles in Liver and Spleen" Majumdar et al., Radiology 1988; 169:653–655.

"Bone Marrow Imaging Using Stir at 0.5 and 1.5T" Kendall M. Jones et al., Magnetic Resonance Imaging vol. 10 pp. 169–176 1992.

"Transverse Relaxation (1/T2) of Solvent Protons Induced by Magnetized Spheres and Its Relevance to Contrast Enhancement in MRI" Koenig et al., Investigative Radiology vol. 23 9–88 pp. S224–S228 (1988).

"Structure Activity Relationship of Magnetic Particles as MR Contrast Agents" Thomassen et al., Magnetic Resonance Imaging vol. 9 pp. 255–258. (1991).

"Cardiovascular MR Imaging with Iron Oxide Particles: Utility of A superparamagnetic Contrast Agent (List continued on next page.)

OTHER PUBLICATIONS and the Role of Diffusion in Signal Loss" Rozenmann et al., Radiology 1990; 175:655-659.

"Ferrite Particles: A superparamagnetic MR Contrast AGent for Enhanced Detection of Liver Carcinoma" Sanjay Saini et al., Radiology 1987; 162:217-222.

"MR Imaging of Splenic Matastases: Ferrite-Enhanced Detection in Rats" Reissleder et al., AJR 149:723-726, Oct. 1987.

"MR Receptor Imaging: Ultrasmall Iron Oxide Particles Targeted to Asialoglycoprotein Receptors" Ralph Weissleder et al., AJR 155:1161-1167 Dec. 1990.

"Hepatic Cirrhosis and Hepatitis: MR Imaging Enhanced with Superaramagnetic Iron Oxide" Guillermo Elizondo et al., Radiology 1990; 174:797-801.

"Hepatic Micrometastases in the Rat: Ferrite-enhanced MR Imaging" Yuk-Ming Tsang et al., Radiology 1988; 167:21-24.

"Superparamagnetic Iron Oxide-enhanced MR Imaging: Pulse Sequence Optimization for Detection of Liver Cancer" Fretz et al., Radiology 1989; 172:393-397.

"Magnetoferritin: In Vitro Synthesis of a Novel Magnetic Protein" Fiona C. Meldrum et al., Science vol. 257 Jul. 24, 1992 pp. 522-523.

"Iron Oxide-Enhanced MR Imaging of the Liver and Spleen: Review of the First 5 Years" Ferrucci et al., AJR 155:943-950 Nov. 1990.

"Non-invasive quantitation of liver iron-overload by magnetic resonance imaging" Kaltwasser et al., British Journal of Haematology 1990 74 360-363.

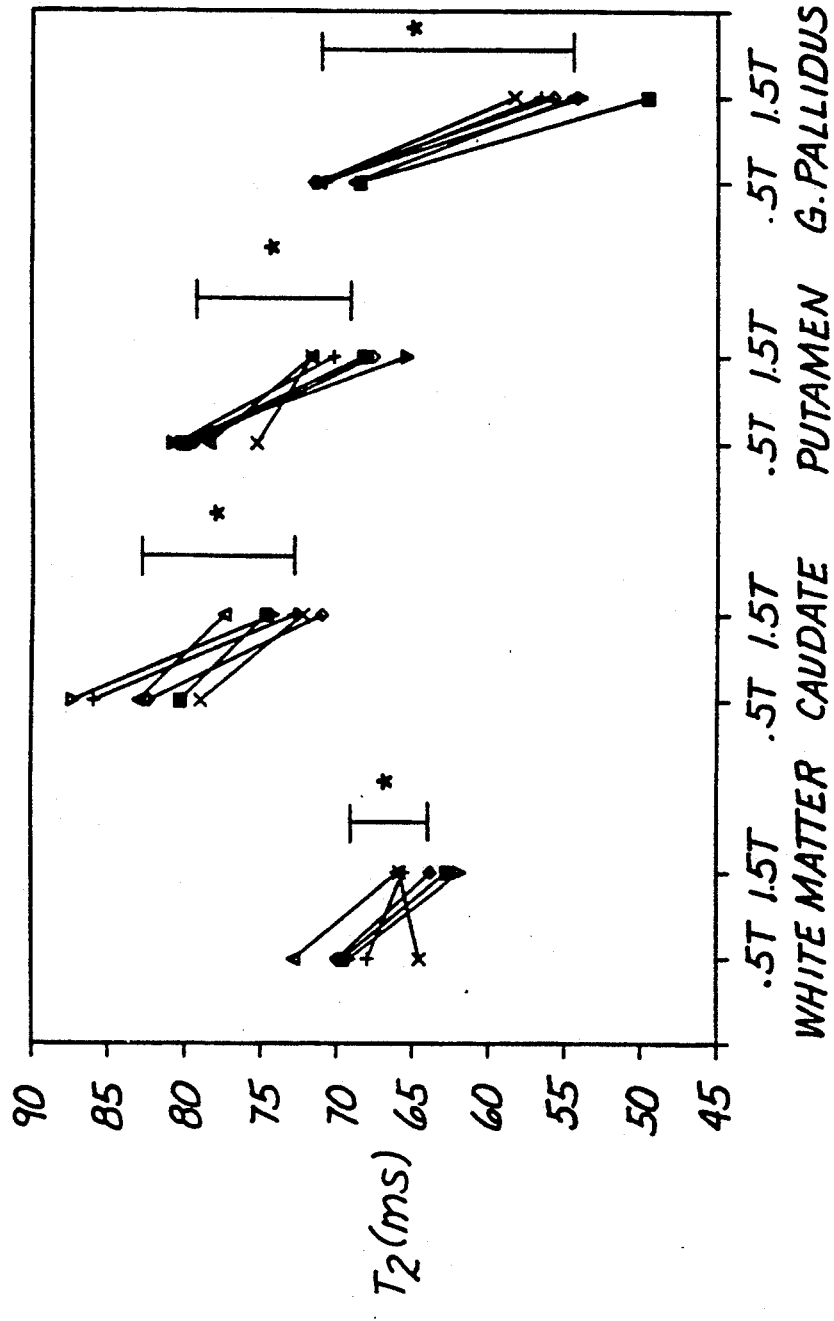

METHOD FOR QUANTITATIVELY MEASURING AND MAPPING STORED IRON IN TISSUE USING MRI

BACKGROUND OF THE INVENTION

1. Field of the Invention

The invention relates to the field of the use of magnetic resonance in medicine to measure iron stores in tissue, and in particular to quantitatively and specifically measure in vivo ferritin and closely related substances in tissue.

2. Description of the Prior Art

During the past decade, a number of studies have implicated iron as a central culprit in various diseases including some cancers. A genetic disease, hemochromatosis, which causes excessive accumulations of iron in tissue and which can be fatal, is estimated to occur or to be at risk in an estimated 1.4 million Americans. The accumulation of iron stores in tissue has also been implicated in various studies in liver damage, arthritis, diabetes, impotence, heart failure and various neurological disorders such as Alzheimer's and Parkinson's disease. Iron stores is understood to mean ferritin or ferritin like proteins, which is the biological form for storage of iron.

The deleterious effects of excessive iron stores levels in tissue is thought to be related to its ability to catalyze the production of hydroxil radicals from other free radicals which naturally occur within the human body as well as direct toxic effects of iron itself. The largest part of iron stores in human tissue normally occurs in a complex protein called ferritin, the storage form of iron. Free radicals such as superperoxides, as well as other substances which occur in the body can remove the iron from ferritin, where it is harmless, to catalyze the formation of more destructive radicals which are believed to be linked to the above disease states.

However, one of the major stumbling blocks in attaining a clear idea how ferritin or other iron stores molecules relate to disease states has been the inability to quantitatively and specifically measure ferritin in vivo. Prior art biochemical assays in many cases can only be conducted postmortem or through biopsy. All biopsies, but especially brain biopsies are subject to risk, expensive, and traumatic to the patient.

The noninvasive use of magnetic resonance imaging to measure iron stores is well known, but remains controversial and is by no means universally accepted or considered well established. The nuclear magnetic resonance of hydrogen atoms bound in water in biological tissue can be directly measured. The radio frequency signal produced by relaxational hydrogen atoms in a nuclear magnetic resonance experiment will decay with two characteristic decay rates or periods $T_1$ or $T_2$. The $T_1$ decay is based upon spin-lattice couplings, while the $T_2$ decay period is based upon spin-spin couplings among the protons. These decay periods are affected by the molecular environment in which the hydrogen is present. Throughout the remainder of the specification the symbols $T_2$ will be used to refer to the $T_2$ relaxation time. The relaxation rate corresponding to $T_2$ is denoted by the symbol, $R_2$. The relation between the $T_2$ relaxation time and the $R_2$ relaxation rate is given by $R_2 = 1000/T_2$. Therefore, either parameter may be used interchangeably through this algebraic equivalence, or for that matter any uniquely related third parameter or measure may used if more practical. Currently, most nuclear magnetic resonance imaging (MRI) equipment provides a readout in terms of $T_2$ and therefore, $T_2$ will be used as the preferred measure. The presence of magnetic (e.g. paramagnetic, ferromagnetic, etc.) materials such as iron in tissue has been found to have a material effect upon the $T_2$. Iron, in turn, occurs naturally throughout human tissue and in blood.

Brain extrapyramidal grey matter nuclei exhibit a lower $T_2$ and this $T_2$ shortening appears to be related to high iron concentrations in these grey matter nuclei, see, Drayer et. al., AJNR 7, 373 (1986); Duguid et. al., J. Ann.Neurol 20, 744 (1986); Coffey et.al., J. Neuropsych. Clin. Neurosci. 1, 400 (1989); Schaffert et. al., Neurology 39, 440 (1989) and Bizzi et. al., Radiology 177, 59 (1990). The capability of MRI to quantify iron levels in vivo remains controversial as some investigators report a lack correlation with postmortem tissue iron levels in $T_2$ values, see, Chen et. al., Radiology 173, 521 (1989); and Brooks et. al., J. Neurol. Neurosurg., Psychiatry 52, 108 (1989). Nevertheless, multiple lines of evidence support an association between $T_2$ shortening and tissue iron levels. First, many investigators observed $T_2$ shortening in disorders with known abnormal iron accumulation in the brain and liver, see, Drayer, Radiology 173, 311 (1989); Duguid et. al., J. Ann. Neurol 20, 744 (1986); Coffey et. al., J. Neuropsych. Clin. Neurosci. 1, 400 (1989); Brasch et. al., Radiology 150, 767 (1984); Leung et. al., J. Comput. Assist. Tomogr. 8, 446 (1984); Stark et. al., Radiology 154, 137 (1985); Gomori et. al., J. Comput. Assist. Tomogr. 9, 972 (1985); Gomori et. al., Radiology 157, 87 (1985); Johnston et. al., Am. J. Med. 87, 40 (1989); and Thulborn et. al., AJNR 154, 291 (1990). Second, some postmortem studies report that $T_2$ shortening corresponded to increased iron levels, see, Duguid et. al., J. Ann. Neurol 20, 744 (1986); Coffey et. al., J. Neuropsych. Clin. Neurosci. 1, 400 (1989); and Schaffert et. al., Neurology 39, 440 (1989). Third, age-related increase in brain iron in normal humans has also been demonstrated in vivo using magnetic resonance techniques, see, Aoki et. al., Radiology 172, 381 (1989).

The extrapyramidal system contains the highest concentration of iron in the brain; signal levels between one-and-a-half to almost two times as high as that in liver, see, Hallgren et. al., J. Neurochemistry 3, 41 (1958). The largest single fraction of tissue iron is stored in the iron storage protein, ferritin, see, Hallgren et. al., J. Neurochemistry 3, 41 (1958); and Hill et. al., *Brain Iron: Neurochemical and Behavioral Aspects*, chapter 1, Taylor and Francis (1988).. Ferritin molecules are comprised of a multisubunit protein shell surrounded by crystalline core of hydrous ferric oxide that may include up to as many as 4500 ferric iron atoms. The association between high iron levels and central nervous system damage has been observed in a variety of disorders. Involvement of iron in the process of lipid peroxidation has been suggested as a common mechanism for such damage, see, Park et. al., Neurology 25, 1172 (1975); Sadeh et. al., Ann. Neurol. 7, 286 (1980); and Kim et. al., Neurology 31, 774 (1981). Therefore, methods that can quantify specific physiological iron compounds, such as ferritin in vivo, could be clinical value in disorders involving brain extrapyramidal nuclei, Duguid et. al., J. Ann. Neurol 20, 744 (1986); Coffey et. al., J. Neuropsych. Clin. Neurosci. 1, 400 (1989); Schaffert et. al., Neurology 39, 440 (1989) and other tissues.

It is known that ferritin has a strong magnetic effect that results in marked $T_2$ shortening in vitro and in vivo. Therefore, nuclear magnetic resonance relaxation times have been used to visualize evolution of hemorrhages, Gomori et. al., J. Comput. Assist. Tomogr. 11, 684-690 (1987).

It is known that the enhancement of iron-related contrast as seen in magnetic resonance images is dependent on field strengths, but it has not been previously known that the field dependence could be used in any way to be specific to ferritin or that it was a quantitative measure of the ferritin that would have any clinical utility, see, Schenck et. al., Book of Abstracts, Volume 1, Society of Magnetic Resonance in Medicine (1989).

The invention is directed to a method which utilizes the field dependence of ferritin induced $T_2$ shortening as a way of specifically identifying and quantifying iron stores levels. What is needed, therefore, is a methodology whereby specific identification and quantitative in vivo measurements of patients can be made reliably, and wherein measurements of ferritin and closely related iron containing proteins or substances can be selectively or specifically made.

BRIEF SUMMARY OF THE INVENTION

The invention is a method of specifically detecting iron stores in vivo using magnetic resonance comprising the steps of measuring in vivo the relaxation time $T_2$ of at least one predetermined position within a subject at a first magnetic field strength. A second in vivo measurement is made of the relaxation time $T_2$ at the predetermined position within the subject at a second, different magnetic field strength. A field dependent $T_2$ signal, T, is generated from the difference of the two $T_2$ relaxation times, namely $T_2$ measured at the first and second field strengths. The change, T, is a specific indication of the iron stores in vivo.

The method further comprises the step of correlating T to a specific quantitative measure of the iron stores in vivo. This step correlates T obtained in vivo to a quantitative measure of ferritin. The signal, T, is measured in terms of differences in $T_2$ in milliseconds, in terms of $R_2$ relaxation rates ($1000/T_2$ seconds$^{-1}$), or any other related measure which would render the field dependent shortening, T, observable according to best practice.

The steps of measuring and differencing are repeated at a plurality of predetermined points to create a multidimensional map of the iron stores in vivo. Preferably, a visual two-dimensional display is generated.

In the illustrated embodiment, the step of measuring $T_2$ at the first field strength is performed on a first magnetic resonance imaging instrument and the step of measuring $T_2$ at the second field strength is measured on a second magnetic resonance imaging instrument. The method further comprises the step of immobilizing the subject in at least one standardized position. The step of immobilizing comprises the step of positioning the subject within the magnetic resonance imaging instruments to assume a predetermined position of each of the instruments with respect to at least one standard anatomical reference point with respect to the subject.

The steps of measuring are repeated within a selected tissue region within the subject in order obtain minimum statistical deviation of measurements within the tissue region. Another way to measure is to measure the entire region and take the $T_2$ differences on a point-by-point basis followed by calculation of a statistical measure for the entire region. Still another way to measure is to make a statistical histogram of the $T_2$ measurements in each region and then edit out those portions of the histogram which appear to be anomalous.

In another embodiment, the step of measuring $T_2$ in vivo measures artificially disposed nonbiological magnetic agents or contrast agents introduced into the subject. The method also includes the step of measuring $T_2$ in vitro of artificial nonbiological magnetic agents for the purpose of developing, testing or calibrating such agents.

The invention is also characterized as a method for obtaining a visual image of iron stores in vivo in tissue comprising the steps of scanning a predetermined region of a subject to determine $T_2$ at each point within the region at a first magnetic field strength. The field in which the subject is disposed may be created by a first magnetic resonance imaging instrument. The predetermined region of the subject is scanned a second time to determine $T_2$ at each point within the region at a second magnetic field strength. The subject may be disposed in a second magnetic resonance imaging instrument or in a second field created by the first magnetic resonance imaging instrument. An enhanced image, T, of the region based on the tissue content of ferritin or ferritin-like substances in the subject is generated by subtracting $T_2$ at the first field strength from $T_2$ obtained at the second field strength at each point within the region. The difference between $T_2$ at the two field strengths provides an enhanced image, T, of the relative amount of iron stores in vivo.

The method further comprises the step of correlating T at each point within the region to a measure of T in at least one phantom of known concentration of iron stores. This allows the iron stores to be quantified in tissue at each point within the region. The tissue which is quantified may be in vivo or may be in vitro, such as would be the case for biopsied tissue samples. The method further comprises the step of displaying the quantitative measure of the iron stores in vivo at each point in the region to form a graphic depiction of the quantitative measure of iron stores.

The method further comprises the step of visually identifying different tissue types as normal or abnormal based upon visual contrast provided by T which is indicative of the tissue iron stores.

The method further comprises the step of disposing nonbiological magnetic agents into the subject wherein presence of the nonbiological magnetic agents is quantitatively determinable in vivo.

The method further comprises the step of identifying tissue origin within the subject by matching the quantitative measure of iron stores within the tissue to the tissue origin, such as in cancer identification, cell differentiation and other applications tracing cell development or origination.

The invention can be better visualized by considering the following drawings wherein like elements are referenced by like reference numerals.

BRIEF DESCRIPTION OF THE DRAWINGS

FIG. 3 is a graph showing the period $T_2$ as measured in vivo in the human brain at 1.5 and 0.5 Tesla field strengths in different regions of the brain.

Figure 1:
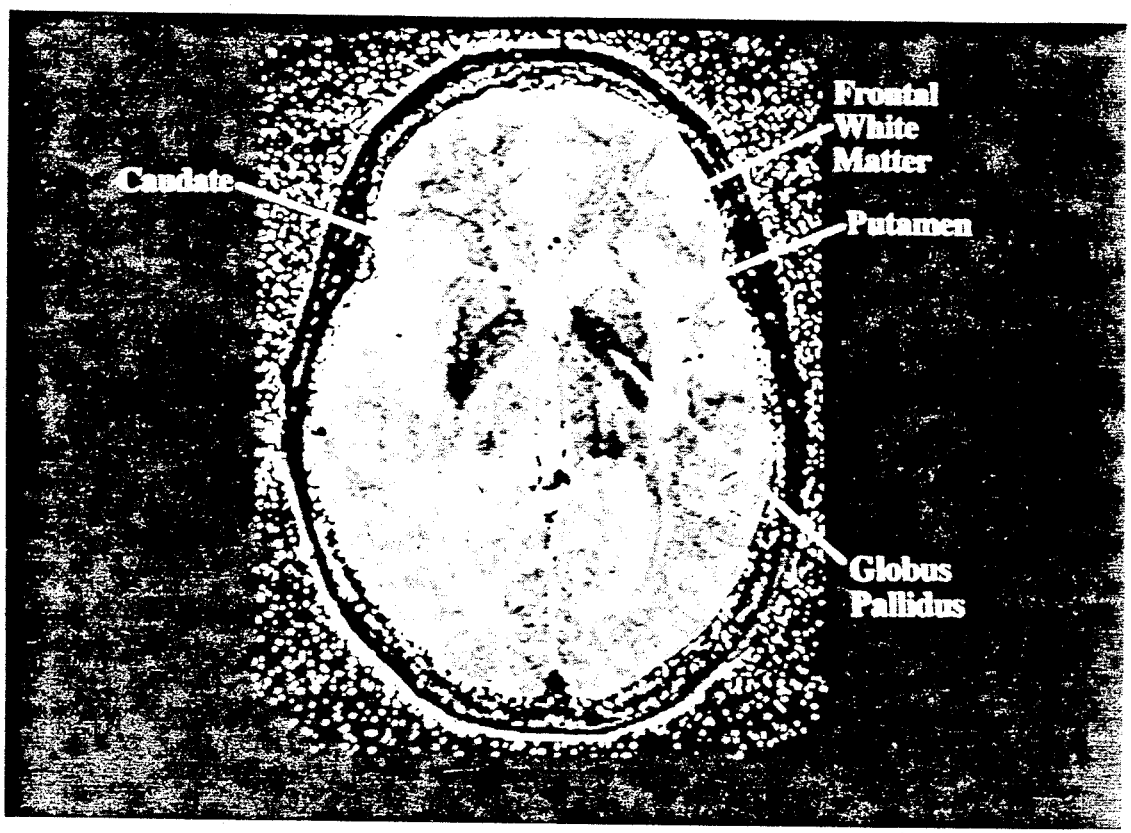
FIG. 1 is a displayed $T_2$ image of the putamen and globus pallidus acquired in an MRI human brain scan.

The invention and its various embodiments may now be understood by turning to the following detailed description.

DETAILED DESCRIPTION OF THE PREFERRED EMBODIMENTS

The invention provides a specific measure of iron stores in vivo using magnetic resonance imaging. The $T_2$ of tissue in both lower-to-mid field strength magnetic resonance imaging instruments and a higher field strength instrument is evaluated. $T_2$ obtained by the higher field strength instrument is subtracted from $T_2$ obtained by the lower field strength instrument or vica versa. This difference, T, obtained in vivo is then correlated with a quantitative measure of the iron stores in vivo in the scanned tissue. A two-dimensional or multi-dimensional map of the scanned tissue is then constructed on the basis of T to visually identify different tissue types as being normal or abnormal, either through a visual determination based on gray scales or a numeric comparison based on quantitative measure. The introduction of artificial or nonbiological substances as opposed to natural ferritin, is permitted for further diagnostic use.

Iron levels vary widely among different human tissues. Since iron in the free state can be extremely toxic, all cells produce iron storage proteins to minimize the toxicity. Abnormal iron metabolism is believed to be involved in many disorders. This is especially true in chronic disorders of aging and may be related to the fact that the body has no active mechanism to excrete excess iron. The invention is a noninvasive risk-free way of obtaining specific quantitative data on body iron metabolism which has utility in diagnosis, prognosis and the monitoring of treatment of many disorders ranging from tumor identification to problems associated with normal aging.

It has been well established in magnetic resonance studies that $T_2$ is a quantifiable tissue parameter that can be shortened by magnetic substances such as iron stores and other physical properties of tissue such as water content and packing structure of the tissue. As a result, variations in $T_2$ are usually not regarded as specific measures of iron concentration at either the cellular or tissue level.

The present invention overcomes the nonspecificity of $T_2$ measurements and also quantifies the various metabolic states of iron in body tissue. The nonspecificity of the $T_2$ measurements is overcome by subtracting the $T_2$ value obtained at a higher field strength from that obtained at a lower field strength. In the present embodiment, the difference, T, in $T_2$ is determined using two different field strength instruments and is a specific measure of the concentration of iron storage protein with iron containing core structures the same as or similar to ferritin.

Therefore, according to the invention an MRI scan may be made and recorded for a section of tissue, such as the human brain. If desired, the measured values of $T_2$ can be graphically displayed in terms of a gray scale at each point in the brain section as an intermediate result. Thereafter, a second scan at the same section is made at different field strength and recorded. The second scan can also be displayed as an intermediate result if desired. The two recorded scans of $T_2$ are then point-by-point or structure-by-structure differenced to obtain a quantitative and enhanced image, T, which is specific to ferritin concentrations. The quantitative difference, T, in $T_2$ can be stored in a file and output or displayed as a two dimensional map of difference values or presented as a multidimensional array of numbers. The physician may, therefore, visually see ferritin in the tissue and quantitatively correlate as well as qualitatively map the relationship of ferritin concentrations to neurologic disorders and other disease states.

In the present state of the art, scanning the subject at different field strengths requires positioning the subject in two different magnetic resonance imaging machines or scanners so that the tissue imaged and the magnetic field conditions, except for field strength, in the two scanners are identical or as close to identical as can practically achieved. Normally, the two scans are made sequentially in one measurement session, although it is within the scope of the invention that the scans can also be made at different times and places with the data output between the scans combined at a later time. The scans will need to be calibrated as described below in order to be used together. It is believed that ferritin concentrations will generally not change dramatically within a patient during normal time periods of a few days or weeks unless there is active intervention of some specific agent.

With the present availability of the clinical MRI machines, the MRI field strength cannot be quickly changed in a single machine through the magnitudes which are desired in order to measure the field strength dependence of $T_2$ for determination of ferritin. Thus, two magnetic resonance imaging (MRI) machines are used in sequence, one at each field strength. It is expressly contemplated that the engineering arts will progress to the point where the process described here will be practical in a single MRI machine and therefore both one or multiple MRI scanning units are expressly within the scope of the claims. In vitro measurements of $T_2$ at different field strengths within a single MRI machine is presently practical.

In the case where two MRI machines are used, the patient's head is localized or semi-immobilized in a fixture and the fixture repeatedly positioned in the scanning field between the two scanners. Second, the $T_2$ measurement is made in such a manner that measurements of tissues, which are not of interest, are minimized. The measurements are oriented so that $T_2$ measurements are derived, for example, from gray matter within the human brain while blood vessels, white matter, cerebral spinal fluid, and the like are avoided in order to obtain a more representative measure of the grey matter. Still further, in order to obtain a quantitative value of $T_2$, the area which is measured is magnified for better visualization and repeated measurement samples are taken at different locations in the structure to obtain better representation of the tissue of interest. Finally, the $T_2$ data received from the scan from one scanner at the lower field strength and the second scanner at the higher field strength are matched through software data manipulation so that the outputs of the two scanners can be superimposed; including datagraphic corrections to reposition the images for maximal superimposition of the images even though the original scanned subject may not have been identically positioned between the scan in the first scanner and the scan in the second scanner. Included within the invention is a computer controlled search among the sections scanned between the two units to find the best datagraphic match on a section-by-section basis even after all other corrections to standardize the outputs have been made.

An example of the use of the invention will illustrative.

EXAMPLE I

The invention is first demonstrated in vitro. Although calibration of the field dependent $T_2$ shortening to obtain iron or ferritin concentrations could be made using theoretical calculations based on first principles, accurate clinical calibration must be made empirically using a phantom in order to compensate for measurement artifacts. Generally, to calibrate the output the phantom is prepared with ferritin in a concentration expected in the brain. $T_2$ is measured at the two field strengths which are selected. Interpolation of other iron concentrations from the phantom values are then made to determine the relationship of iron concentration to T. If the relationship is believed or found to be nonlinear, then the method of the invention is practiced by constructing a calibration curve based on a range of multiple iron phantoms.

In Example I the phantoms are comprised of 4 ml plastic vials containing a mixture of 1.2 percent agarose gel (Type II Medium EEO, Sigma Chemical Company, St. Louis, Mo. and 1.0 mM cupric sulfate (anhydrous cupric sulfate, J. T. Baker Chemical Company, Phillipsburg, N.J. This preparation was chosen as the baseline gel in order to approximate iron-free gray matter in the human brain. It is possible in fact that the gel is not perfectly free of some iron contamination. The $T_2$ relaxation time in this baseline gel preparation was measured at approximately 83 milliseconds. Therefore, the value was above the upper range of basal ganglia $T_2$ observed in adult human brains which is approximately 45 to 75 milliseconds using a 1.5 Tesla MRI scanner as described below. The field strengths of 0.5 and 1.5 Tesla were used in the example only as illustrative points and its is entirely within the contemplation of the invention that other field strengths could be used, including a difference in field strengths or a pair of field strengths which would optimize the T measure.

Using the baseline gel, a phantom using ferritin, apoferritin. Apoferritin is the ferritin molecule with the iron substantially removed, and ferric chloride were prepared and measured at the two field strengths. Three concentrations of iron in the form of ferric chloride were used, namely 5, 10 and 20 milligrams of iron per 100 grams of gel. These iron concentrations where chosen to approximate the iron concentrations observed in postmortem normal human brain of 4, 9 and 21 milligrams per iron per 100 grams of tissue for white and cortical gray matter, caudate nucleus, and globus pallidus, respectively.

A single batch of horse spleen ferritin, containing a average of 2900 iron atoms per molecule of ferritin, as determined by Sigma Chemical Company of St. Louis, Mo. based upon atomic absorption spectrometry, was used to prepare a second set of three phantoms containing ferritin concentrations that match the iron content of the three free iron phantoms above.

A single batch apoferritin containing trace amounts of iron contaminant (0.0031% as determined by Sigma using atomic absorption) was used to prepare a third set of three apoferritin phantoms containing the same molar concentrations as the ferritin phantoms.

Figure 2:
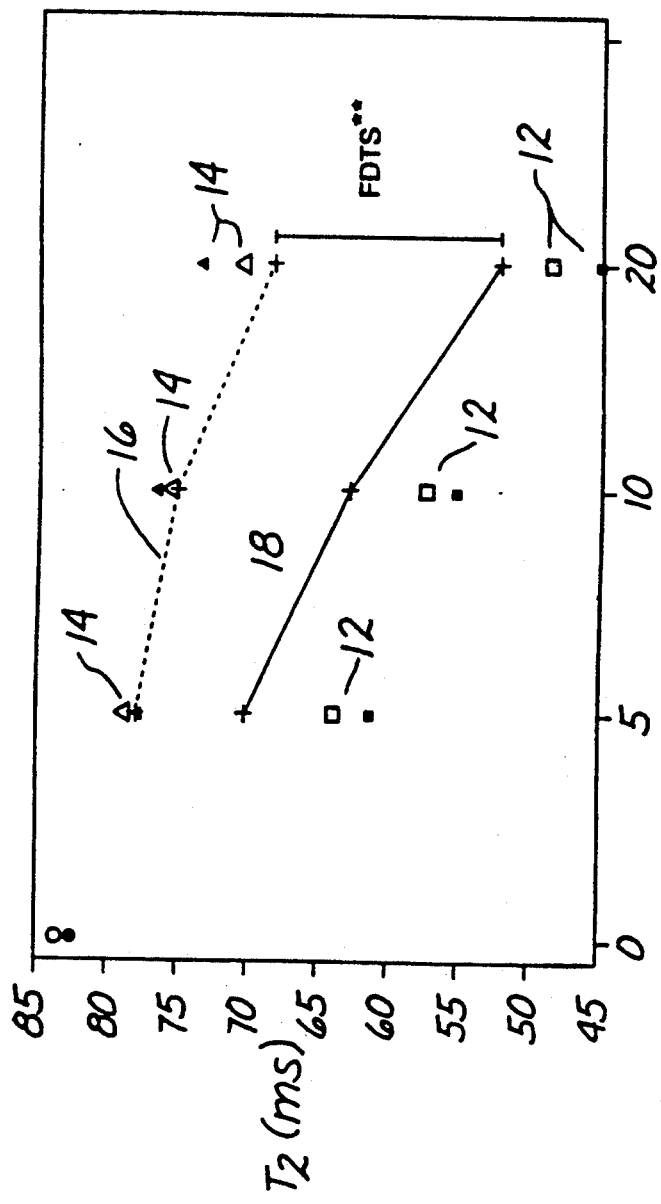
FIG. 2 is a graph showing the period $T_2$ as measured in vitro against ferritin and apoferritin concentrations as measured in 1.5 and 0.5 Tesla fields.

All the phantoms were scanned at room temperature in both the 0.5 Tesla and 1.5 Tesla instruments. Scanning at other temperatures, such as body temperatures, may also be practiced. FIG. 2 illustrates the $T_2$ measurements for free iron, apoferritin, and the baseline gel. The data points for the two field strengths of the gel is shown by points 10, the open circle being the 0.5 Tesla measurement and the solid circle being the 1.5 Tesla measurement. $T_2$ is plotted on the vertical scale in FIG. 2 in milliseconds and was approximately the same at the two field strengths for the gel.

The results for free iron are shown by the data points 12 at the three concentrations and are depicted again by an open square and a solid square showing the low field and high field $T_2$, respectively. Again, the difference between the two is small and varies only slightly as a concentration of iron varies. The results depicted with free iron are nonbiological since free iron never occurs in living tissue in the concentrations used in the example, which are approximately twelve orders of magnitude too high. The free iron concentration was chosen, however, to match the non-heme iron concentration found in brain structures. The nonbiological phantom of free iron was chosen only to illustrate the dramatic effect that ferritin has on T. The results obtained for apoferritin are shown between the open triangle and solid triangle of points 14.

In dramatic contrast, the ferritin phantoms show a wide difference in $T_2$ as depicted by the low field measurement depicted by dotted line 16 and the high field measurement depicted by solid line 18. Not only is there a significant difference in $T_2$ at each concentration, the difference, T, increases as the concentration of ferritin increases. This increase is specific to ferritin and allows the concentration to be quantitatively measured.

The change, T, attained at the two field strengths is strongly related to ferritin concentration. The correlation, which is dramatically illustrated in FIG. 2, is found to be statistically relevant, whereas no statistical relevance is found with respect to any variations in concentrations in apoferritin, the baseline gel, or with other molecule involved in iron metabolism such as transferrin or apotransferrin. Note, unlike the ferritin, apoferritin, transferrin and apotransferrin that the amounts of free iron in the iron phantoms are not physiologic.

EXAMPLE II

In the second example, a human in vivo measurement involved six adult subjects, five males and one female, between the ages of 21 and 30. All subjects were scanned using the same two clinical Picker MRI instruments as used in the phantom studies operating at 0.5 Tesla and 1.5 Tesla as summarized in FIG. 2.

The position of the subject's head in each of the MRI scanners was maintained during each scanning session by creating a semirigid mold of the back and sides of the subject's head. The head-positioning mold was then physically moved and the patient's head was repositioned in the same mold in the second scanner. In addition, the head position was further defined by aligning anatomical landmarks of the subject's head with marks made on the head mold itself.

In both the in vivo and in vitro measurements, the position of the actual MRI images were standardized. In the in vivo experiment, the positioning was standardized by first obtaining a mid-sagittal pilot image and then placing the inferior edge of the slice-select grid for the axial images at the apex of the fourth ventricle. In the in vitro experiment, the mid-sagittal pilot image was used to place the middle slice of the slice-select grid for the axial images at the midpoint of the phantom tubes. All other further protocols and procedures were carried out exactly for both the 0.5 Tesla and 1.5 Tesla studies.

In both the in vivo and in vitro MRI examples, identical Carr Purcell Meiboom Gill two spin-echo sequences (TR=2500, TE=20,90) with two signals averaged, at 192 gradient steps, 3 millimeter slice thickness, and 25 centimeter field of view were used. It is expressly contemplated that other sequences could be used, such as gradient echo sequences that quantify $T_2^*$. Any sequence that included a $T_2$ influence could be used, since the differencing step enhances the field dependant effects. All further calculations and data extraction procedures again were carried out exactly for both the 0.5 and 1.5 Tesla studies. The $T_2$ values were calculated using system software and the $T_2$ data was extracted. $T_2$ was calculated for each voxel by an automated algorithm from the two (TE=20,90) signal intensities of the two spin-echo sequences to produce gray scale encoded $T_2$ maps of the brain and the phantoms as demonstrated in the photograph of FIG. 1.

The $T_2$ maps are magnified four times to simplify the actual data recording and to avoid areas that would produce partial volume effects, such as small focal brain lesions or the margins of the nuclei and phantoms. The phantom $T_2$ data was obtained from a single slice containing all the phantoms. The brain $T_2$ data was obtained from two slices. The slice containing the largest portion of the putamen and globus pallidus was used to obtain the $T_2$ data for those regions, and the slice superior to it was used to obtain the $T_2$ data of the caudate and white matter. The mean $T_2$ values for a standard 32 voxel (0.32 square centimeter) area containing the most homogeneous section of each brain region or phantom was recorded. The position of greatest homogeneity within each brain section or phantom was determined by repeatedly moving the 32 voxel circle and choosing the mean $T_2$ value which had the smallest standard deviation.

In Example II the $T_2$ data from the individual subjects are displayed in FIG. 3. Data from the six human subjects was analyzed using a 4×2×2 within-subjects repeated measures analysis of variance (MANOVA). The subject-factors were brain region, namely frontal white matter, caudate, putamen and globus pallidus, left or right hemisphere and field strength, namely 0.5 Tesla and 1.5 Tesla. A highly significant correlation was found between the brain region and the field strength while no significant effect was found involving the two brain hemispheres.

Table 1 shown below illustrates that the reduction in $T_2$ at the high field strength was statistically significant in all four brain regions using a t-test for correlated samples. Pairwise contrasts were computed, comparing the field dependent $T_2$ shortening across the four brain regions. These contrasts were used as pooled estimates of error for the overall repeated measures (ANOVA) for all tests.

TABLE 1

| Brain $T_2$ Values at Two Field Strengths | | | |
|---|---|---|---|
| Brain Region | Field | Mean $T_2$ Value | T |
| frontal white matter | .5 Tesla | 69.00 | |
| | 1.5 Tesla | 64.29 | 4.71 |
| caudate | .5 Tesla | 82.97 | |
| | 1.5 Tesla | 73.71 | 9.26 |
| putamen | .5 Tesla | 79.07 | |
| | 1.5 Tesla | 69.09 | 9.98 |
| globus pallidus | .5 Tesla | 70.31 | |
| | 1.5 Tesla | 54.77 | 15.54 |

The data demonstrates that field dependent $T_2$ shortening can be observed and quantified both in vitro and in vivo with clinical magnetic resonance instruments operating at field strengths of 0.5 and 1.5 Tesla. The data shows that the field dependent $T_2$ shortening observed in phantom experiments using ferritin occurs both qualitatively and quantitatively in vivo and that the field dependent $T_2$ shortening of various brain structures correlates with published nonheme iron concentrations.

Together the in vivo and in vitro results provide evidence that $T_2$ values which are obtained with high field clinical instruments are dependent on the ferritin content of the tissue and that the field dependent $T_2$ shortening is useful as a specific quantitative measure of the ferritin content of the tissue. It should be noted however that the iron loading in individual ferritin molecules may vary, namely from as little as no iron atoms per molecule to 4500 iron atoms per molecule. In Example I the ferritin phantoms had a fixed average iron loading.

It is also expressly contemplated that the invention measures and could distinguish both ferritin molecular concentrations as well as iron loading within the ferritin molecule by using phantoms with varied iron loading according to the procedures described above.

The specificity of field dependent $T_2$ shortening for ferritin is further demonstrated when the field dependent $T_2$ shortening of white matter is compared to the field dependent $T_2$ shortening of basal ganglia gray matter. White matter has high rates of field independent $T_2$ relaxation processes as indicated by the low $T_2$ values obtained for this tissue was both 0.5 and 1.5 Tesla instruments. Thus, sources of field independent $T_2$ shortening is eliminated by subtracting the $T_2$ obtained in high field instrument from that obtained in the low field instrument.

There are multiple possible explanations for the field dependent $T_2$ shortening produced by ferritin. One explanation is that the field inhomogeneity created by the heterogeneous distribution of paramagnetic ferric iron atoms in the ferritin core shorten the observed $T_2$ to a greater extent in higher than in lower field strength instruments. Other explanations involve special properties that may be unique to this kind of iron oxide in crystalline form. The small microcrystalline ferric oxide structure of the ferritin molecule may exhibit a variety of magnetic behaviors like ferromagnetism, antiferromagnetism and superparamagnetism. Regardless of the mechanism producing the field dependent $T_2$ shortening, the data demonstrates that the iron in the form found in ferritin contributes markedly and specifically to this effect.

The data also demonstrates that the method is sensitive to quantifying differences of tissue iron stores. Statistically significant medical differences between white matter and caudate field dependent $T_2$ shortening and the difference between white matter and caudate iron is approximately 5 milligrams iron per 100 grams of tissue. This difference in ferritin iron stores can be discerned in vivo according to the invention.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. The following claims are, therefore, to be read to include not only the combination of elements which are literally set forth, but all equivalent elements for performing substantially the same function in substantially the same way to obtain substantially the same result. The claims are thus to be understood to include what is specifically illustrated and described above, what is conceptionally equivalent, and also what essentially incorporates the crux of the invention.

For example, it is to be expected and it is within the scope of the invention that the use of different instruments with different and possibly more optimum field strengths that the ones described here will improve the sensitivity of the technique. Since ferritin is present in all tissues, it must be understood that the method can be utilized in other organs other than brain or nerve tissue, especially ones with relatively high iron concentrations like the liver, spleen and muscle.

It is, therefore, anticipated than the method of the invention may be used to advantage in vivo in any situation where imaging of iron stores in tissue at millimeter resolution with MRI techniques is desired.

The central nervous systems is at especially high risk for damage from free radical neurotoxic processes catalyzed by iron. Thus, increased iron levels may have significant pathophsiological consequences. The involvement of free radical neurotoxic processes has been postulated for a variety of age-related neuropsychiatric disorders such as Parkinson's disease, Alzheimer's disease, tardive dyskinesia and possible the process of aging itself. Since iron levels are known to increase with age, the involvement of iron in such disorders will be significantly benefited by using the present in vivo method. In addition, MRI techniques could be used to monitor iron chelating treatments which are currently used in transfusion hemosiderosis patients and have been successfully tried in Alzheimer's disease patients. The treatment may be monitored by obtaining serial MRI evaluations of the patients during their treatment according to the invention.

By eliminating field independent contributions to $T_2$ shortening, the approach of subtracting $T_2$ data obtained in high field instruments from data obtained in low field instruments provides specific and quantitative in vivo biochemical information while maintaining the millimeter resolution available through current imaging technology. It is expected that further work in this area will refine and verify the specificity of iron in the form found in ferritin as a sole or major contributor to field dependent $T_2$ shortening and that the quantitative relationship between ferritin levels and field dependent $T_2$ shortening will become better established and accepted.

The invention also becomes an analytic instrument for the production and testing of nonbiological agents or substances which can act as magnetic markers in MRI studies. The use of synthetic ferritin or related synthetic forms of the ferritin core as such a marker for use in clinical studies and treatment is expressly contemplated.

We claim:

1. A method of specifically detecting iron stores in vivo using magnetic resonance comprising the steps of:
    measuring in vivo a parameter which is a function of $T_2$ of at least one predetermined position within a subject at a first magnetic field strength;
    measuring in vivo a parameter which is a function of $T_2$ at said predetermined position within said subject at a second magnetic field strength, said second magnetic field strength being unequal to said first magnetic field strength; and
    generating a field dependent $T_2$ signal, T, by differencing $T_2$ measured at said first and second field strengths, T being a specific indication of said iron stores in vivo.

2. The method of claim 1 further comprising the step of correlating T to obtain a specific quantitative measure of said iron stores.

3. The method of claim 2 wherein said step of correlating correlates T to a quantitative measure of ferritin in vivo, in vitro or both.

4. The method of claim 1 wherein T is derived from measurements of $T_2$ relaxation times.

5. The method of claim 1 wherein said steps of measuring T is derived from measurements of relaxation rates ($R_2$).

6. The method of claim 1 wherein said steps of measuring and differencing are repeated at a plurality of predetermined points to create a multidimensional map of said iron stores in vivo.

7. The method of claim 1 wherein said step of measuring $T_2$ at said first field strength is performed on a first magnetic resonance imaging instrument and wherein said step of measuring $T_2$ at said second field strength is measured on a second magnetic resonance imaging instrument.

8. The method of claim 7 further comprising the step of semi-immobilizing said subject during said steps of measuring in a standardized position.

9. The method of claim 6 wherein said step of measuring $T_2$ at said first field strength is performed on a first magnetic resonance imaging instrument and wherein said step of measuring $T_2$ at said second field strength is measured on a second magnetic resonance imaging instrument, and further comprising the step of semi-immobilizing said subject in a standardized position during said steps of measuring.

10. The method of claim 9 where said step of measuring comprises the step of measuring only tissue which is homogeneous with respect to type.

11. The method of claim 10 where said step of measuring is repeated within a selected tissue region within said subject in order obtain minimum statistical deviation of measurements within said tissue region.

12. The method of claim 10 where said step of measuring within said tissue region comprises the step of placing the same tissue region in the same poition in the magnetic field at said first and second field strengths and wherein said step of generating generates T from substantially identical tissue regions.

13. The method of claim 11 wherein said step of measuring within said tissue region comprises the step of positioning said subject within said magnetic resonance imaging instruments to assume a predetermined position of each of said instruments with respect to a standard anatomical reference point with respect to said subject.

14. The method of claim 1 wherein said step of measuring T in vivo of said subject measures artificially disposed nonbiological magnetic agents introduced into said subject.

15. The method of claim 1 wherein said step of measuring T measures artificially disposed nonbiological magnetic agents in vitro.

16. The method of claim 1 wherein said step of measuring T measures tissue in vitro.

17. A method for obtaining a visual image of iron stores in vivo in tissue comprising the step of:
scanning a predetermined region of a subject to determine at each point within said region a parameter which is a function of $T_2$ within said region at a first magnetic field strength created by a magnetic resonance imaging instrument;
scanning said predetermined region of said subject to determine at each point within said region a parameter which is a function of $T_2$ within said region at a second magnetic field strength created by a magnetic resonance imaging instrument; and
generating an enhanced image of said region of said subject by subtracting $T_2$ obtained at said first field strength from $T_2$ obtained at said second field strength at each point within said region to obtain T, said enhanced image providing an enhanced measure of said iron stores.

18. The method of claim 17 where said first and second magnetic field strengths are produced by separate magnetic resonance imaging instruments.

19. The method of claim 17 where said first and second magnetic field strengths are produced by the same magnetic resonance imaging instrument at different times.

20. The method of claim 17 further comprising the step of correlating T in vivo at each point within said region to a quantitative measure of iron stores.

21. The method of claim 17 further comprising the step of visually identifying different tissue types as normal or abnormal based upon visual contrast provided by said tissue iron stores.

22. The method of claim 18 further comprising the step of visually identifying different tissue types as normal or abnormal based upon visual contrast provided by said tissue iron stores.

23. The method of claim 17 further comprising the step of disposing nonbiological magnetic agents into said subject wherein presence of said nonbiological magnetic agents is quantitatively determinable in vivo.

24. The method of claim 17 wherein said step of scanning at said first magnetic field strength and said step of scanning at said second magnetic field strength are performed in different magnetic resonance imaging instruments and further comprising the steps of data-processing the scans produced by said different magnetic imaging instruments to graphically and subtractively superimpose one upon the other within said scanned region to generate a graphic display of T.

25. The method of claim 17 further comprising the step of identifying tissue origin within said subject by matching said quantitative measure of iron stores within said tissue to said tissue origin.

26. The method of claim 17 where said step of generating said enhanced image provides an enhanced measure of iron stores in vivo, in vitro or both.

27. The method of claim 2 where said step of correlating T comprises the step of obtaining a quantitative measure of iron loading within ferritin molecules.

* * * * *